United States Patent
Lam et al.

(10) Patent No.: US 11,517,468 B2
(45) Date of Patent: Dec. 6, 2022

(54) ADHESIVE OSTOMY WAFER HAVING A LINER REMOVED TO EXPOSE ADHESIVE

(71) Applicants: Peter Kwok Hing Lam, Frederiksberg C (DK); Matthew Laws, London (GB); Liam O'Brien, London (GB); Michael Hansen, Gilleleje (DK); Birthe Vestbo Andersen, Espergaerde (DK); Kristoffer Hansen, Naerum (DK); Steffen Kongensbjerg Larsen, Copenhagen (DK)

(72) Inventors: Peter Kwok Hing Lam, Frederiksberg C (DK); Matthew Laws, London (GB); Liam O'Brien, London (GB); Michael Hansen, Gilleleje (DK); Birthe Vestbo Andersen, Espergaerde (DK); Kristoffer Hansen, Naerum (DK); Steffen Kongensbjerg Larsen, Copenhagen (DK)

(73) Assignee: Coloplast A/S, Humlebaek (DK)

(*) Notice: Subject to any disclaimer, the term of this patent is extended or adjusted under 35 U.S.C. 154(b) by 1238 days.

(21) Appl. No.: 15/983,105

(22) Filed: May 18, 2018

(65) Prior Publication Data
US 2018/0263805 A1  Sep. 20, 2018

Related U.S. Application Data

(63) Continuation of application No. 13/993,077, filed as application No. PCT/DK2011/050491 on Dec. 16, 2011, now Pat. No. 9,999,535.

(30) Foreign Application Priority Data

Dec. 17, 2010  (DK) ............................ PA 2010 70553
Jan. 25, 2011  (DK) ............................ PA 2011 70041

(51) Int. Cl.
*A61F 5/443*  (2006.01)
*A61F 5/44*  (2006.01)

(52) U.S. Cl.
CPC ............ *A61F 5/4404* (2013.01); *A61F 5/443* (2013.01)

(58) Field of Classification Search
CPC combination set(s) only.
See application file for complete search history.

(56) References Cited

U.S. PATENT DOCUMENTS 2,048,392 A * 7/1936 Koenig .................. A61F 5/445
                                                        604/342
4,723,952 A * 2/1988 Esposito ................ A61F 5/449
                                                        604/338

(Continued)

*Primary Examiner* — Guy K Townsend
(74) *Attorney, Agent, or Firm* — Coloplast Corp., Coloplast A/S; Nick Baumann

(57) ABSTRACT

An adhesive ostomy wafer has a liner removed to expose adhesive and thus ready the adhesive ostomy wafer for adhesion to a user. The adhesive ostomy wafer includes a backing layer providing a distal surface of the adhesive ostomy wafer that is oriented to face away from skin of the user during use, an adhesive layer deposited onto the backing layer, with the adhesive layer providing a proximal surface of the adhesive ostomy wafer, an opening formed through the backing layer and the adhesive layer, with the opening adapted to fit around a stoma of the user, and a reinforcement structure located between the distal surface and the proximal surface of the adhesive ostomy wafer.

15 Claims, 2 Drawing Sheets

(56) References Cited

U.S. PATENT DOCUMENTS

| | | | | |
|---|---|---|---|---|
| 5,722,965 A * | 3/1998 | Kuczynski | A61F 5/443 | 604/338 |
| 6,106,507 A * | 8/2000 | Botten | A61F 5/448 | 604/338 |
| 6,673,056 B2 * | 1/2004 | Metz | A61F 5/448 | 604/338 |
| 6,790,200 B2 * | 9/2004 | Fenton | A61F 5/445 | 604/338 |
| 6,869,422 B2 * | 3/2005 | Fenton | A61F 5/445 | 604/338 |
| 2002/0088080 A1 * | 7/2002 | Fenton | A61F 5/445 | 604/338 |
| 2003/0004477 A1 * | 1/2003 | Nielsen | A61F 5/448 | 604/336 |
| 2003/0088219 A1 * | 5/2003 | Metz | A61F 5/448 | 604/339 |
| 2004/0193122 A1 * | 9/2004 | Cline | A61F 5/448 | 604/332 |
| 2004/0193123 A1 * | 9/2004 | Fenton | A61F 5/448 | 604/344 |
| 2004/0230170 A1 * | 11/2004 | Fenton | A61F 5/445 | 604/336 |
| 2005/0054997 A1 * | 3/2005 | Buglino | A61F 5/448 | 604/332 |
| 2007/0055205 A1 * | 3/2007 | Wright | A61F 15/004 | 424/447 |
| 2007/0219514 A1 * | 9/2007 | Strobech | A61F 5/441 | 604/339 |
| 2007/0282284 A1 * | 12/2007 | Mullejans | A61F 5/441 | 604/333 |
| 2008/0097361 A1 * | 4/2008 | Fabo | A61F 5/445 | 604/338 |
| 2008/0300556 A1 * | 12/2008 | Fenton | A61F 5/4404 | 604/339 |
| 2009/0216208 A1 * | 8/2009 | Leisner | A61F 5/448 | 219/121.64 |
| 2009/0299309 A1 * | 12/2009 | Fenton | A61F 5/443 | 604/339 |
| 2011/0098665 A1 * | 4/2011 | Bach | A61L 24/001 | 604/317 |
| 2011/0213322 A1 * | 9/2011 | Cramer | A61F 5/443 | 604/332 |
| 2011/0218507 A1 * | 9/2011 | Andersen | A61F 5/445 | 604/338 |
| 2015/0018790 A1 * | 1/2015 | Lam | A61F 5/443 | 604/344 |

* cited by examiner

ADHESIVE OSTOMY WAFER HAVING A LINER REMOVED TO EXPOSE ADHESIVE

FIELD OF THE INVENTION

An ostomy wafer comprising a proximal surface in an axial direction facing the user during use provided with an adhesive layer, a distal surface in the axial direction facing away from the user during use provided with a backing layer, coupling means for attaching a collection bag, an opening having an inner radial boundary defining a stoma receiving opening, and an outer radial boundary defining the peripheral edge of the ostomy wafer.

BACKGROUND OF THE INVENTION

In connection with surgery for a number of diseases in the gastro-intestinal tract, one of the consequences in many cases is that the patient is left with an abdominal stoma, such as a colostomy or an ileostomy in the abdominal wall for the discharge of visceral contents. The discharge of visceral contents cannot be regulated at will. For that purpose, the user will have to rely on an appliance to collect the material emerging from such an opening in a bag, which is later emptied and/or discarded at a suitable time.

An ostomy appliance may be in the form of a two-piece appliance comprising an ostomy wafer and a collecting bag which may be coupled to and un-coupled from each other through a coupling, or a one-piece appliance where the ostomy wafer is permanently coupled to a collecting bag and when the collecting bag is replaced the ostomy wafer is removed from the skin surface of the user.

The stoma is usually located close to the abdominal area of the user, or it may sometimes be located elsewhere if the abdominal area is not suited for having the stoma. The stoma usually exits via an opening the abdominal wall of the user and is fixed in position by suturing a part of the stoma to the opening in the abdominal wall. This means that the area surrounding the stoma may be subjected to movements in the abdominal wall due to movements of the user, such as during exercise, bending over, bending backwards, and so on. Furthermore, the area surrounding the stoma is affected by the layers of cutaneous and sub-cutaneous tissue, such as the thickness of the skin and the thickness of fat layers, etc.

SUMMARY OF THE INVENTION

According to the invention, there is provided an ostomy wafer comprising an adhesive layer provided with a proximal surface in an axial direction facing the user during use, a backing layer provided with a distal surface in an axial direction facing away from the user during use, coupling means for attaching a collection bag, an opening having an inner radial boundary defining a stoma receiving opening, an outer radial boundary defining the peripheral edge of the ostomy wafer, wherein the ostomy wafer is provided with a reinforcement structure arranged in an axial direction between the proximal surface and the distal surface and in a radial direction between the inner and outer radial boundary for preventing deformation of the stoma receiving opening in the longitudinal and/or the axial direction during use.

This means that the reinforcement structure will increase the stiffness of the ostomy wafer, so that when the ostomy wafer is applied to the area surrounding the stoma and this area is subjected to movements, or deformation, the ostomy wafer may resist the movements and maintain its substantial shape in the longitudinal direction. In addition, the ostomy wafers ability to bend from its initial substantially flat shape is reduced and/or the ostomy wafers ability to compress in the axial direction is reduced, ensuring that the ostomy receiving opening substantially maintains its shape and thus reducing the risk that the ostomy receiving opening will strangle the stoma due to movements subjected to the area surrounding the stoma. Furthermore, the reinforcement structure reduces the risk that the movement of the area surrounding the stoma will deform the skin surface of that area in such a way that the adhesive will detach at least partly from the skin surface. Such a detachment will increase the risk that a the adhesive wafer may be subjected to a leak, as any detachment of the adhesive in the area close to the stoma receiving opening will increase the risk that fluid or solid excrements may come into contact with the adhesive and weaken the adhesive bond between the skin surface and the adhesive surface.

Furthermore, a reinforcement structure may protect the ostomy wafer from excessive bending/folding of the adhesive layer, as bending/folding of the adhesive layer may lead to failure of the adhesive layer as the adhesive may crack across and/or along the bending line or folding line.

In one embodiment of the present invention, the reinforcement structure may be in the form of a closed line shape, such as a ring, an ellipse or a polygon. By providing the reinforcement structure in a closed line shape, the reinforcement structure may surround the ostomy receiving opening in its entirety and provide an increased rigidity in the longitudinal direction and in the axial direction. A shape such as the ring will provide a substantially uniform increase in stiffness or rigidity in both the longitudinal direction and in the axial direction, where a ring that surrounds the stoma receiving opening reduces the ostomy wafers ability to deform from its flat shape and reduces its ability to be compressed in the axial direction along all directions in the longitudinal direction and in the axial direction. This means that no matter in what direction it is bent from its substantially flat shape, it may provide the same deterrent from deformation. Furthermore, no matter in what direction a compression is made in the axial direction, it may provide the same deterrent from deformation in all directions.

In one embodiment, where the reinforcement structure is in the form of an ellipse, meaning that the reinforcement structure stretches to a larger length in a first axial direction than it does in a second axial direction that is substantially at a right angle to the first axial direction, it is possible to align or arrange the elliptical shape in such a way, allowing the ostomy wafer to deform more in the second axial direction than in the first axial direction, and thereby providing the ostomy wafer with a non-uniform rigidity. This allows the user to arrange the ostomy wafer in a specific orientation onto the skin surrounding the stoma based on his or her preference so that the deformation is controlled in a specific direction.

In one embodiment of the present invention, the reinforcement structure may be in the form of a reinforcement member that is arranged on the distal surface of the ostomy wafer. The reinforcement member may be welded/adhered using a line edge or the whole abutting surface of the reinforcement member.

In one embodiment of the present invention, the reinforcement structure may be in the form of at least two discrete reinforcement members arranged on opposing sides of the stoma receiving opening in the radial direction. By arranging the at least two discrete reinforcement members on opposing sides of the stoma receiving opening, it is possible to increase the rigidity of the ostomy wafer along some parts of the longitudinal direction, allowing full flexibility of the wafer in other parts of the longitudinal direction. I.e. if two discrete reinforcement members are arranged on opposed sides in the west and east (as seen on a compass), the ostomy wafer will have an increased rigidity to bend across lines that pass from one reinforcement member to the other while also crossing the stoma receiving opening, while it will remain fully flexible across lines that do not cross the reinforcement members, or in directions close to north and south. This means that if the user has a tendency to bend over in a forwards or backwards manner, and thereby deforming the area surrounding the stoma accordingly in a lateral direction (substantially at a right angle to the bending movement), the ostomy wafer may be arranged so that the reinforcement member reduces the deformation of the ostomy wafer in the lateral direction, while allowing full flexibility in a direction that is at a right angle to the lateral direction.

The ostomy wafer may be provided with three or more discreet reinforcement members that are arranged in a preferred pattern around the stoma receiving opening, should the user require reinforcement in a specific fashion based on the user's normal or preferred activities.

In one embodiment of the present invention, the reinforcement structure may be embedded within the adhesive layer of the ostomy wafer. By embedding the reinforcement structure within the adhesive layer it is possible to produce the ostomy wafer in a simple way by forming the adhesive layer and thus embedding the reinforcement structure in a single step, and thus simplifying the production process from a situation where the reinforcement structure is attached to the ostomy wafer as a subsequent step to forming the adhesive layer. As the adhesive layer is the layer which is attached to the skin of the user, using a skin contacting surface of the adhesive layer, the reinforcement structure does not change the shape or structure of the skin contacting surface, and thus it is possible to retain a smooth flat skin contacting surface. The smooth flat surface may ensure that the entire skin contacting surface is in contact with the skin, and thus reducing the risk that parts of the skin contacting surface detaches from the skin and causes a leakage.

Further, if the reinforcement structure is embedded in the adhesive layer, the reinforcement structure does not form part of the backing layer, so that the reinforcement structure does not interfere with the distal surface of the ostomy wafer and any coupling between the ostomy wafer and a collecting bag, i.e. a mechanical, adhesive or permanent coupling, is not affected by the reinforcement member, and the distal surface is maintained substantially smooth and flat. Thus, an adhesive coupling would have a smooth flat distal surface for the adhesive coupling between the bag and the wafer, which reduces the risk of a leakage forming in the coupling area. For a mechanical coupling, the mechanical coupling member which is attached to the distal surface of the ostomy wafer may be attached in a normal manner to the distal surface.

In one embodiment of the present invention, the reinforcement structure may be embedded within the backing layer of the ostomy wafer. The advantages of embedding the reinforcement structure within the backing layer is that the structure does not interfere with the skin contacting surface or the distal surface of the ostomy wafer, similar to that where it is embedded within the adhesive layer.

In one embodiment of the present invention, the reinforcement structure may be embedded between the adhesive layer and the backing layer of the ostomy wafer. Thus, the reinforcement structure may be arranged in between the two layers and not form part of either layer. In another embodiment, the reinforcement structure may be arranged such that the reinforcement structure is embedded in both layers, i.e. that the structure forms parts of both layers. The advantages of embedding the reinforcement structure between the adhesive layer and the backing layer is that the structure does not interfere with the skin contacting surface or the distal surface of the ostomy wafer, similar to that where it is embedded within the adhesive layer and in the backing layer.

In one embodiment of the present invention, the reinforcement structure is positioned at a radial distance from the stoma receiving opening of 0-50% of the radial distance from the inner boundary to the outer radial boundary, or more specifically between 1-40% of the radial distance from the inner boundary to the outer radial boundary, or even more specifically between 2-30% of the radial distance from the inner boundary to the outer radial boundary, or especially between 5-20% of the radial distance from the inner boundary to the outer radial boundary. The positioning of the reinforcement structure will alter the flexibility of the ostomy wafer. A reinforcement structure that stretches across a large area increases the rigidity of the ostomy wafer in a longitudinal direction, while a reinforcement member that is positioned to be close to the stoma receiving opening may ensure that the opening's ability to compress in an axial or radial direction is reduced.

In one embodiment of the present invention, the reinforcement structure is made of a material that is more rigid than the adhesive layer and/or the backing layer. A more rigid material increases the rigidity of the ostomy wafer in the areas where the reinforcement structure is arranged.

In one embodiment of the present invention, the reinforcement structure is made of a thermoplastic material, a metallic material, a woven material, a non-woven material, a fibrous material or any material combination thereof.

In one embodiment of the present invention, the reinforcement structure is made of a material that provides a greater rigidity along the radial axis than the adhesive and/or backing layers of the ostomy wafer.

In one embodiment of the present invention, the reinforcement structure is made of a material that provides a greater rigidity along the axial direction than the adhesive and/or backing layers of the ostomy wafer.

DETAILED DESCRIPTION OF THE DRAWINGS

Figure 1:
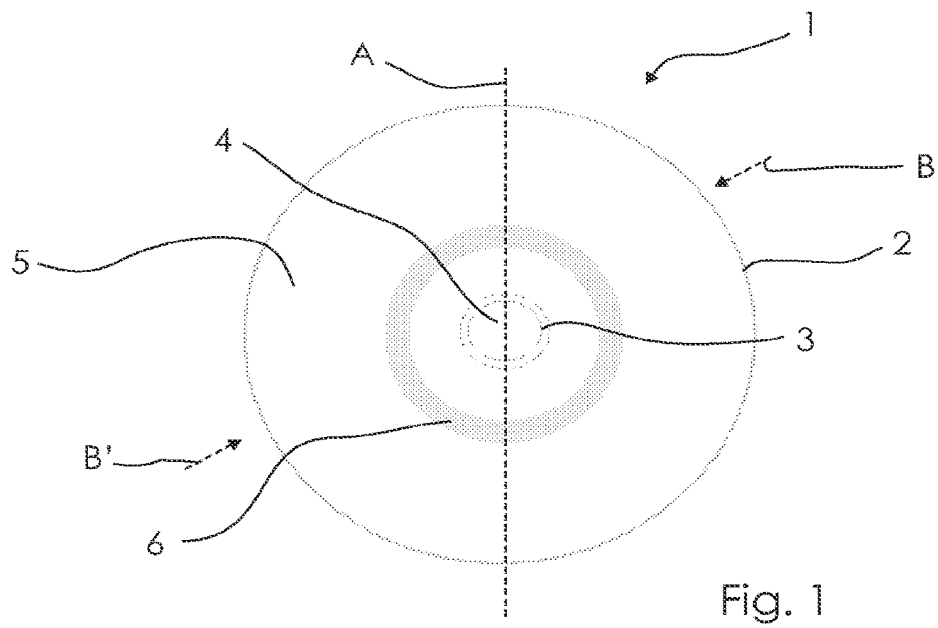
FIG. 1 is a top view of an ostomy wafer according to the present invention.

FIG. 1 shows a top view of an ostomy wafer 1 according to the present invention having a peripheral edge 2 and a stoma receiving opening 4 defined by an inner radial boundary 3. The distal surface 5 of the ostomy wafer is provided with a backing layer which stretches from the peripheral edge 2 to the inner radial boundary 3. On the opposite side (not seen), the ostomy wafer is provided with an adhesive layer (7 in FIG. 2) having a skin contacting surface (8 in FIG. 2).

The distal surface 5 of the ostomy wafer 1 is provided with a reinforcement structure in the form of a stiffening ring 6 that may be permanently attached to the distal surface of the ostomy wafer. The stiffening ring 6 reduces the flexibility of the ostomy wafer 1, ensuring that the ostomy wafer will resist to the bending forces that occur when the user's stomach folds due to bending, while softer adhesive constructions will fold or bend due to the stomach folding.

If a folding operation is performed on the ostomy wafer 1 along longitudinal axis A, the stiffening ring 6 will provide a force that resists the folding action, ensuring that undue stretching or compression (depending on the direction of the folding action) will occur in the adhesive layer of the ostomy wafer. Likewise, if a compression force is applied to the ostomy wafer in the axial or radial direction B and/or in the opposite direction B', the stiffening ring will provide resisting force in the opposite directions, ensuring that the ostomy receiving opening 4 will not deform due to the compression forces.

Figure 2:
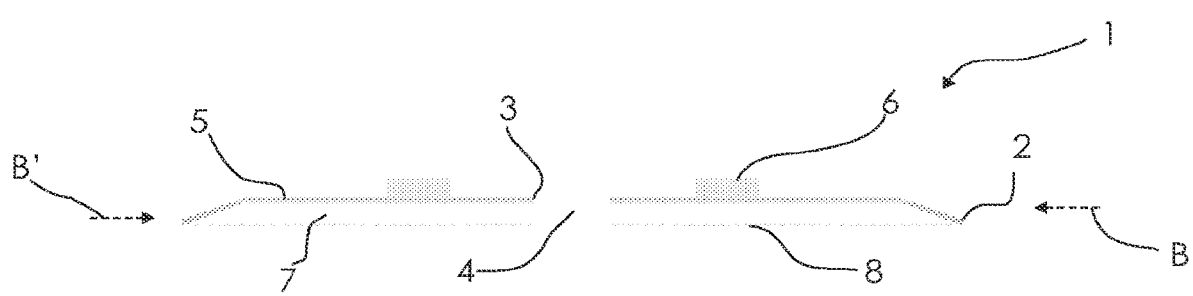
FIG. 2 is a side cross sectional view of the ostomy wafer in FIG. 1
Figure 3:
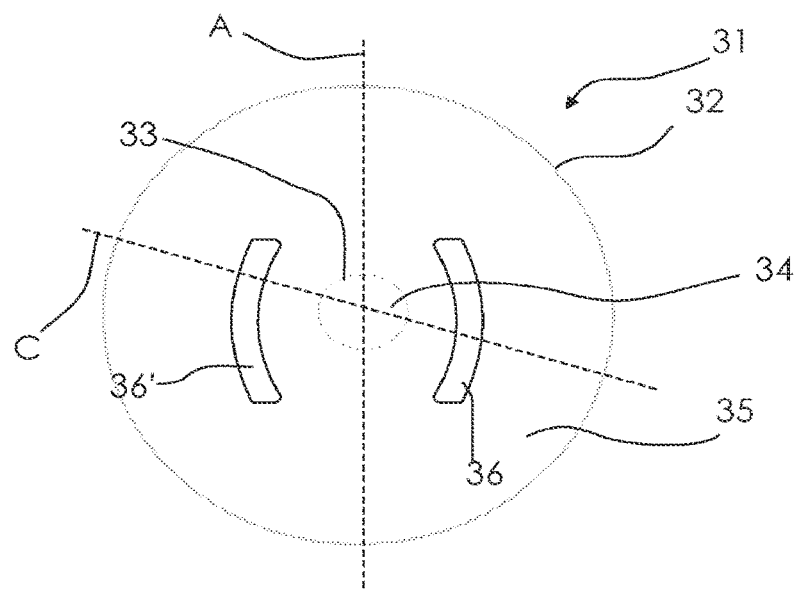
FIG. 3 is a top view of an ostomy wafer according to the present invention having two reinforcement members.

FIG. 3 shows an alternative embodiment of an ostomy wafer 31 to that shown in FIG. 1 and FIG. 2, where the ostomy wafer has a peripheral edge 32 and a stoma receiving opening 34 defined by an inner radial boundary 34. The distal surface 35 of the ostomy wafer is provided with a backing layer which stretches from the peripheral edge 32 to the inner radial boundary 33. On the opposite side (not seen), the ostomy wafer is provided with an adhesive layer (8 in FIG. 2) having a skin contacting surface (9 in FIG. 2).

The distal surface 35 of the ostomy wafer 31 is provided with two discrete reinforcement members 36, 36' that are placed on opposite sides of the stoma receiving opening, in the area between the inner radial boundary 34 and the peripheral edge 32 of the ostomy wafer. By arranging two discrete reinforcement members 36, 36' on opposite sides of the stoma receiving opening, the reinforcement members 36, 36' will provide resisting force when the ostomy wafer is folded across longitudinal axis C, while allowing the ostomy wafer 31 to fold along longitudinal axis A without providing any resisting force. Such an ostomy wafer will provide an increased rigidity in a predetermined longitudinal direction, while allowing the ostomy wafer free bending/folding in longitudinal directions that do not intersect with one or more of the reinforcement members.

Figure 4:
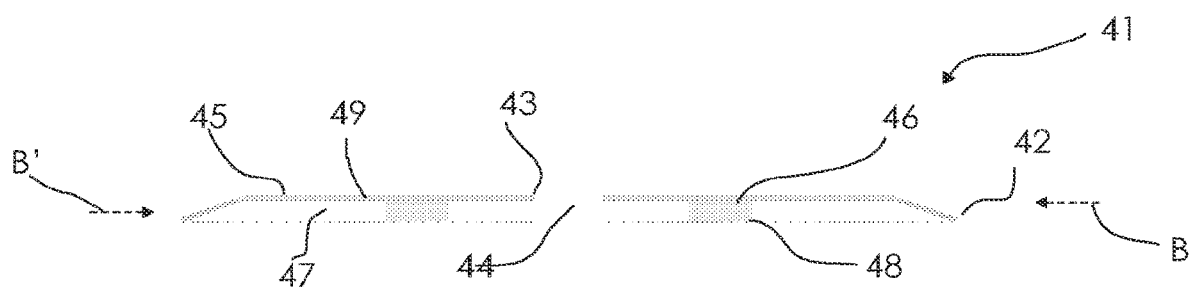
FIG. 4 is a side cross sectional view of an ostomy wafer according to the present invention having a reinforcement structure embedded in the adhesive layer.

FIG. 4 shows a cross sectional view of an ostomy wafer 41 according to the present invention having a peripheral edge 42 and a stoma receiving opening 44 defined by an inner radial boundary 43. The distal surface 45 of the ostomy wafer is provided with a backing layer which stretches from the peripheral edge 42 to the inner radial boundary 43. On the opposite side, the ostomy wafer is provided with an adhesive layer 47 having a skin contacting surface 48.

The ostomy wafer 41 is provided with a reinforcement structure 46 that is embedded into the adhesive layer 47 of the ostomy wafer 41, providing the same structural advantages as the stiffening ring 6 in FIGS. 1 and 2. Thus, the reinforcement structure 46 provides a resisting force against a compressive force applied in the direction B and/or B' and also resist folding forces that are applied in a longitudinal directions (A and C in FIGS. 1 and 3) that intersect the reinforcement structure 46. By embedding the reinforcement structure 46 inside the adhesive layer 47, the distal surface 45 of the ostomy wafer is smooth and uninterrupted across its entire surface 45, which means that a mechanical coupling ring may be attached to the distal surface 45 or an adhesive coupling may be applied to the smooth distal surface 45 for application of a ostomy collection bag. The adhesive coupling will maintain an effective adherence to substantially the entire distal surface 45, and thereby reducing the risk of leakage due to an imperfect seal between the distal surface and the adhesive coupling means of an ostomy collection bag.

The reinforcement structure of the present invention may also be embedded into the backing layer 49 of the ostomy wafer 41, or be arranged between the backing layer 49 and the adhesive layer 47.

Furthermore, the reinforcement structure shown in FIG. 4 may be in the form of two or more discrete reinforcement members, similar to those shown in FIG. 3.

The reinforcement structures disclosed in the present invention may be applied to any ostomy wafer in a one piece or a two piece ostomy appliance, where a one piece ostomy appliance is provided with an ostomy collecting bag that is permanently attached to the distal surface of the ostomy wafer and a two piece ostomy appliance where an ostomy collecting bag is removably attached to the ostomy wafer using a mechanical coupling or an adhesive coupling.

The invention claimed is:

1. An adhesive ostomy wafer having a liner removed to expose adhesive and thus ready the adhesive ostomy wafer for adhesion to a user, the adhesive ostomy wafer comprising:
   a backing layer providing a distal surface of the adhesive ostomy wafer that is oriented to face away from skin of the user during use;
   an adhesive layer deposited onto the backing layer, with the adhesive layer providing a proximal surface of the adhesive ostomy wafer;
   an opening formed through the backing layer and the adhesive layer, with the opening adapted to fit around a stoma of the user; and
   a reinforcement structure located between the distal surface and the proximal surface of the adhesive ostomy wafer, with the reinforcement structure provided as a discrete reinforcement member that does not surround the opening;
   wherein the reinforcement structure reduces flexibility of the adhesive ostomy wafer and adapts the adhesive ostomy wafer to resist bending;
   wherein the reinforcement structure is more rigid than the adhesive layer and the backing layer.

2. The adhesive ostomy wafer of claim 1, wherein the reinforcement structure is arcuate.

3. The adhesive ostomy wafer of claim 1, wherein the reinforcement structure is embedded in the backing layer.

4. The adhesive ostomy wafer of claim 1, wherein the reinforcement structure is embedded in the adhesive layer.

5. The adhesive ostomy wafer of claim 1, wherein the reinforcement structure is sandwiched between the backing layer and the adhesive layer.

6. The adhesive ostomy wafer of claim 1, comprising two discrete reinforcement members with a first discrete reinforcement member located on a first side of the opening and a second discrete reinforcement member that is separated away from the first discrete reinforcement member.

7. The adhesive ostomy wafer of claim 1, comprising at least three discrete reinforcement members, with each discrete reinforcement member separated away from any other of the at least three discrete reinforcement members.

8. The adhesive ostomy wafer of claim 1, wherein the reinforcement structure is separated a first distance from the opening and separated a second distance from an outermost perimeter of the adhesive ostomy wafer.

9. The adhesive ostomy wafer of claim 1, wherein the reinforcement structure is separated a first distance from the opening and separated a second distance from an outermost perimeter of the adhesive ostomy wafer, with the second distance larger than the first distance.

10. The adhesive ostomy wafer of claim 1, wherein the discrete reinforcement member is formed by two arcuate-shaped discs arranged on radially opposite sides of the opening.

11. The adhesive ostomy wafer of claim 1, wherein the two arcuate-shaped discs do not overlap in an axial direction.

12. The adhesive ostomy wafer of claim 1, wherein the distal surface of the backing layer comprises a coupling for a collection bag, the coupling selected from the group consisting of an adhesive coupling, a permanent coupling, and a mechanical coupling.

13. The adhesive ostomy wafer of claim 1, wherein the reinforcement structure is more rigid in a radial direction than either of the adhesive layer and the backing layer in the radial direction.

14. The adhesive ostomy wafer of claim 1, wherein the reinforcement structure is more rigid in an axial direction than either of the adhesive layer and the backing layer in the axial direction.

15. The adhesive ostomy wafer of claim 1, wherein the reinforcement structure projects perpendicular to the backing layer.

* * * * *